(12) United States Patent
Eggert et al.

(10) Patent No.: US 10,561,428 B2
(45) Date of Patent: Feb. 18, 2020

(54) LITHOTRIPSY ANGIOPLASTY DEVICES AND METHODS

(71) Applicant: BOSTON SCIENTIFIC SCIMED, INC., Maple Grove, MN (US)

(72) Inventors: Joel T. Eggert, Plymouth, MN (US); Douglas Dean Pagoria, Forest Lake, MN (US); Raymond Gessler, Roberts, WI (US); Douglas Pennington, Stillwater, MN (US); Daniel J. Foster, Lino Lakes, MN (US); James P. Rohl, Prescott, WI (US); Matthew Hein, Eden Prairie, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 186 days.

(21) Appl. No.: 15/954,194

(22) Filed: Apr. 16, 2018

(65) Prior Publication Data
US 2018/0303504 A1 Oct. 25, 2018

Related U.S. Application Data

(60) Provisional application No. 62/488,387, filed on Apr. 21, 2017.

(51) Int. Cl.
| | |
|---|---|
| *A61B 17/22* | (2006.01) |
| *A61M 25/10* | (2013.01) |
| *A61B 34/00* | (2016.01) |
| *A61L 29/02* | (2006.01) |
| *A61B 17/00* | (2006.01) |

(52) U.S. Cl.
CPC .. *A61B 17/22022* (2013.01); *A61B 17/22004* (2013.01); *A61B 34/73* (2016.02); *A61L 29/02* (2013.01); *A61M 25/10* (2013.01); *A61M 25/104* (2013.01); *A61B 2017/00876* (2013.01); *A61B 2017/22025* (2013.01); *A61B 2017/22051* (2013.01); *A61B 2017/22061* (2013.01);
(Continued)

(58) Field of Classification Search
CPC ........ A61B 17/22022; A61B 17/22004; A61B 34/73; A61B 2017/22051; A61B 2017/22025; A61B 2017/00876; A61B 2017/22061; A61B 2017/22062; A61M 25/10; A61M 25/104; A61M 2205/0272; A61M 2025/1086; A61L 29/02
See application file for complete search history.

(56) References Cited

U.S. PATENT DOCUMENTS

| | | | | |
|---|---|---|---|---|
| 5,611,807 | A | * | 3/1997 | O'Boyle ............ A61B 17/2202 128/898 |
| 6,123,923 | A | * | 9/2000 | Unger ................ A61K 49/0002 424/450 |

(Continued)

*Primary Examiner* — Julian W Woo
(74) *Attorney, Agent, or Firm* — Roeder & Broder LLP; James P. Broder

(57) ABSTRACT

An example method for treating a blood vessel may include disposing a medical device within the blood vessel at a position adjacent to a lesion. The medical device may include an elongate shaft having a distal end region, a balloon coupled to the distal end region, and an iron-containing fluid disposed within the balloon. The method may also include inflating the balloon to a first pressure, delivering a plurality of electromagnetic pulses to the iron-containing fluid, and inflating the balloon to a second pressure greater than the first pressure.

20 Claims, 6 Drawing Sheets

(52) U.S. Cl.
CPC .............. *A61B 2017/22062* (2013.01); *A61M 2025/1086* (2013.01); *A61M 2205/0272* (2013.01)

(56) References Cited

U.S. PATENT DOCUMENTS

| | | |
|---|---|---|
| 8,574,247 B2 | 11/2013 | Adams et al. |
| 8,709,075 B2 | 4/2014 | Adams et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,072,534 B2 | 7/2015 | Adams et al. |
| 9,180,280 B2 | 11/2015 | Hawkins et al. |
| 9,510,887 B2 * | 12/2016 | Burnett .................. A61B 18/02 |

* cited by examiner

LITHOTRIPSY ANGIOPLASTY DEVICES AND METHODS

CROSS REFERENCE TO RELATED APPLICATIONS

This application claims the benefit of U.S. Provisional Patent Application Ser. No. 62/488,387 filed on Apr. 21, 2017, the disclosure of which is incorporated herein by reference.

TECHNICAL FIELD

The present disclosure pertains to medical devices, and methods for manufacturing medical devices. More particularly, the present disclosure pertains to lithotripsy angioplasty devices and methods.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example method for treating a blood vessel is disclosed. The method comprises: disposing a medical device within the blood vessel at a position adjacent to a lesion, the medical device comprising an elongate shaft having a distal end region, a balloon coupled to the distal end region, and an iron-containing fluid disposed within the balloon; inflating the balloon to a first pressure; delivering a plurality of electromagnetic pulses to the iron-containing fluid; and inflating the balloon to a second pressure greater than the first pressure.

Alternatively or additionally to any of the embodiments above, the iron-containing fluid includes iron nanoparticles.

Alternatively or additionally to any of the embodiments above, at least some of the iron nanoparticles have a conical shape.

Alternatively or additionally to any of the embodiments above, delivering a plurality of electromagnetic pulses to the balloon moves at least some of the iron nanoparticles toward a surface of the balloon.

Alternatively or additionally to any of the embodiments above, an electrode is coupled to the shaft and positioned within the balloon, and wherein delivering a plurality of electromagnetic pulses to the iron-containing fluid includes activating the electrode.

Alternatively or additionally to any of the embodiments above, the balloon further comprises a reinforcing member.

Alternatively or additionally to any of the embodiments above, inflating the balloon to a first pressure includes inflating the balloon to a pressure of 3-5 atmospheres.

Alternatively or additionally to any of the embodiments above, inflating the balloon to a second pressure greater than the first pressure includes inflating the balloon to a pressure of 5-9 atmospheres.

A method for treating a blood vessel is disclosed. The method comprises disposing a lithotripsy angioplasty medical device within the blood vessel at a position adjacent to a calcified lesion, the lithotripsy angioplasty medical device comprising: an elongate shaft having a distal end region, a balloon coupled to the distal end region, an iron-containing fluid disposed within the balloon, and an electrode coupled to the shaft; inflating the balloon to a first pressure; transferring force from the balloon to the calcified lesion by delivering electromagnetic pulses with the electrode to activate the iron-containing fluid; and inflating the balloon to a second pressure greater than the first pressure.

Alternatively or additionally to any of the embodiments above, the iron-containing fluid includes iron nanoparticles.

Alternatively or additionally to any of the embodiments above, at least some of the iron nanoparticles have a conical shape.

Alternatively or additionally to any of the embodiments above, transferring force from the balloon to the calcified lesion by delivering electromagnetic pulses with the electrode to activate the iron-containing fluid moves at least some of the iron nanoparticles toward a surface of the balloon.

Alternatively or additionally to any of the embodiments above, the electrode is positioned within the balloon.

Alternatively or additionally to any of the embodiments above, the balloon further comprises a reinforcing member.

Alternatively or additionally to any of the embodiments above, inflating the balloon to a first pressure includes inflating the balloon to a pressure of 3-5 atmospheres.

Alternatively or additionally to any of the embodiments above, inflating the balloon to a second pressure greater than the first pressure includes inflating the balloon to a pressure of 5-9 atmospheres.

A lithotripsy angioplasty medical device is disclosed. The lithotripsy angioplasty medical device comprises an elongate shaft having a distal end region; a balloon coupled to the distal end region; an iron-containing fluid disposed within the balloon; an electrode coupled to the shaft and positioned under the balloon, the electrode being designed to deliver electromagnetic pulses; wherein the balloon is designed to shift between a first unexpanded configuration, a second configuration when the balloon is partially expanded into contact with a target region, and an expanded configuration.

Alternatively or additionally to any of the embodiments above, the iron-containing fluid includes iron nanoparticles.

Alternatively or additionally to any of the embodiments above, at least some of the iron nanoparticles have a conical shape.

Alternatively or additionally to any of the embodiments above, the balloon further comprises a reinforcing member.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
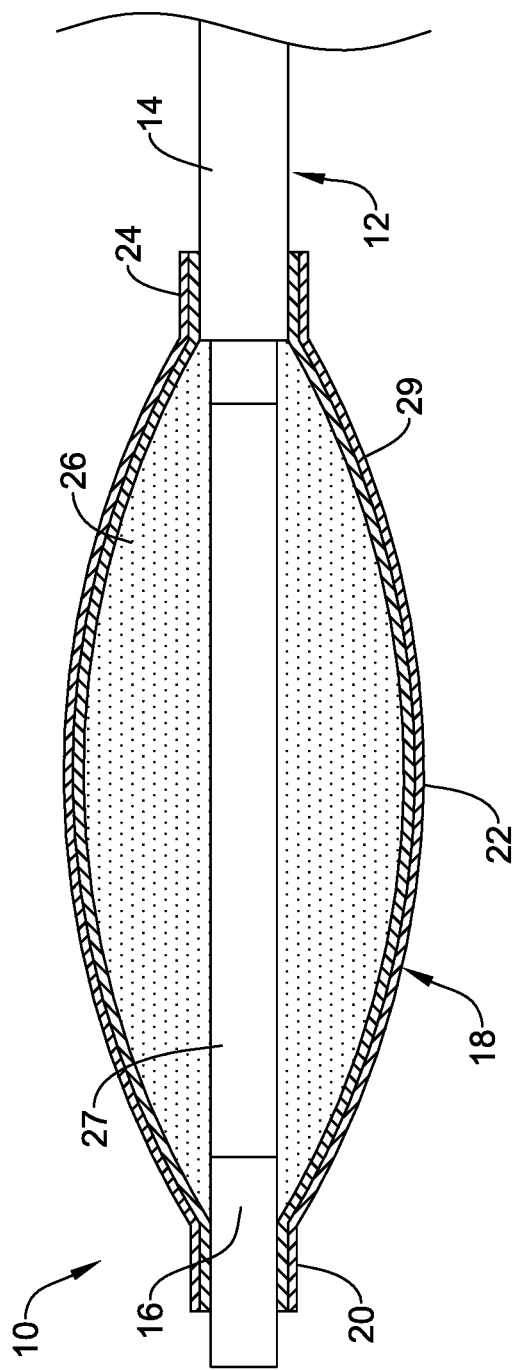
FIG. 1 is a partial cross-sectional side view of an example medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

The use of medical devices for balloon angioplasty may be a desirable method for treating intravascular lesions in a blood vessel. In some instances, calcification along or otherwise adjacent to the vessel wall can complicate an intervention. Disclosed herein are angioplasty devices and methods that are designed to improve the treatment of intravascular lesions. The devices and methods disclosed herein may be described as lithotripsy angioplasty devices/ methods in that the devices may transfer a force to the treatment area to break up the lesion. Some additional details are disclosed herein.

FIG. 1 is a partial cross-sectional side view of an example medical device 10. The medical device 10 may include a catheter shaft 12. In some instances, the catheter shaft 12 may include a first or outer member 14 and a second or inner member 16. A balloon 18 may be coupled to the catheter shaft 12. In some instances, the balloon 18 may include a distal waist 20, a body region 22, and a proximal waist 24. The distal waist 20 may be coupled to the inner member 16. The proximal waist 24 may be coupled to the outer member 14. In at least some instances, the medical device 10 may be an over-the-wire or monorail/single-operator-exchange catheter. Accordingly, the inner member 16 may define a guidewire lumen along at least part of its length. An inflation lumen, in fluid communication with the balloon 18, may be defined between the inner member 16 and the outer member 14. In other instances, the medical device 10 may take the form of a fixed wire catheter. Other constructions are contemplated.

In some instances, the balloon 18 may be structurally reinforced. For example, the balloon 18 may include a reinforcing member 29. The reinforcing member 29 may be a layer of material disposed along the inner surface of the balloon 18, the outer surface of the balloon 18, or both. In some instances, the reinforcing member 29 may include a braid (e.g., a fiber braid), coil, or the like. In some of these and in other instances, the reinforcing member 29 may be disposed along the inner surface of the balloon 18, the outer surface of the balloon 18, or be embedded between two layers of the balloon 18. The reinforcing member 29 may provide additional structural support to balloon 18, which may increase the burst strength of balloon 18. In addition, the reinforcing member 29 may fortify the balloon 18 so that particles (e.g., iron nanoparticles as disclosed herein) may engage the wall surface of the balloon 18 without piercing or otherwise bursting the balloon 18.

In at least some instances, the medical device 10 may be considered a lithotripsy medical device and/or a lithotripsy angioplasty medical device. For the purposes of this disclosure, a lithotripsy angioplasty device may be understood to be a device designed to transfer forces to a target region in a manner that may break apart the target region. In at least some instances, the transfer of forces may occur in a repeated manner with waves or flurries of force that are meant to impact the target region. The repeated force transfers could occur in a regular manner with equally spaced time intervals between transfers, or the force transfers could occur with differing time intervals between transfers. While lithotripsy devices may be commonly associated with ultrasound and/or ultrasonic waves, the lithotripsy angioplasty devices disclosed herein are not meant to be limited to ultrasound devices. Indeed, medical device 10 (as well as other medical devices disclosed herein) may use ultrasound and/or other force generators to transfer force to the target site.

The medical device 10 may include an iron containing fluid 26 disposed within the balloon 18. The iron containing fluid 26 may include a fluid base such as saline, water, or the like, and a plurality of iron particles suspending in or otherwise disposed within the fluid. The iron particles may be considered to be iron nanoparticles (e.g., have a size on the order of about 1-100 nanometers), however this is not intended to be limiting. The iron containing fluid 26 may be designed so that when the balloon 18 (e.g., and/or the iron containing fluid 26) is exposed to a magnetic field, the iron particles within the iron containing fluid 26 may migrate within the balloon 18. In at least some instances, the iron particles may migrate toward the surface of the balloon 18.

When the magnetic field is pulsed, this may cause pulses of movement or force within the balloon 18 that can be transferred to a target site such as a calcified lesion within a vessel. In some instances, magnetostrictive particles (e.g., such as Terfenol-D, Galfenol, or the like) may be added to the iron containing fluid 26. The magnetostrictive particles may enhance or otherwise cause vibration (e.g., vibration of the iron containing fluid 26 within the balloon 18) at an elevated frequency, for example, when the iron containing fluid 26 is exposed to a magnetic field (e.g., a time-varying magnetic field). The magnetic field may be created in a number of different ways. For example, an electrode 27 may be coupled to the shaft 12 (e.g., to the inner member 16) and disposed within the balloon 18. Activation of the electrode 27 may generate the magnetic field. Alternatively, an external magnetic field generator may be utilized to create the magnetic field.

Figure 2:
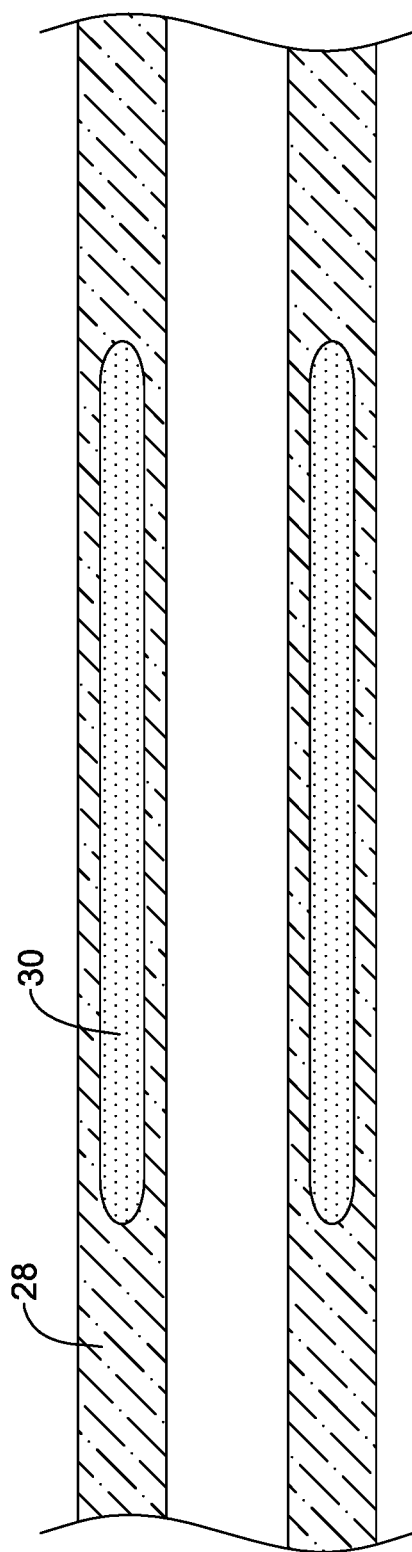
FIG. 2 is a cross-sectional side view of a portion of a blood vessel.

FIGS. 2-6 illustrate the use of the medical device 10. For example, FIG. 2 illustrates an example blood vessel 28. A calcified lesion 30 may be disposed along the blood vessel 28. In this example, the calcified lesion 30 is shown within the wall of the blood vessel 28. However, other arrangements may be seen. For example, portions or all of the calcified lesion 30 may be disposed along an inner surface of the blood vessel 28. In some of these and in other instances, plaque, a stenosis, a fatty deposit, or other types of lesions may also be present within the blood vessel 28.

Figure 3:
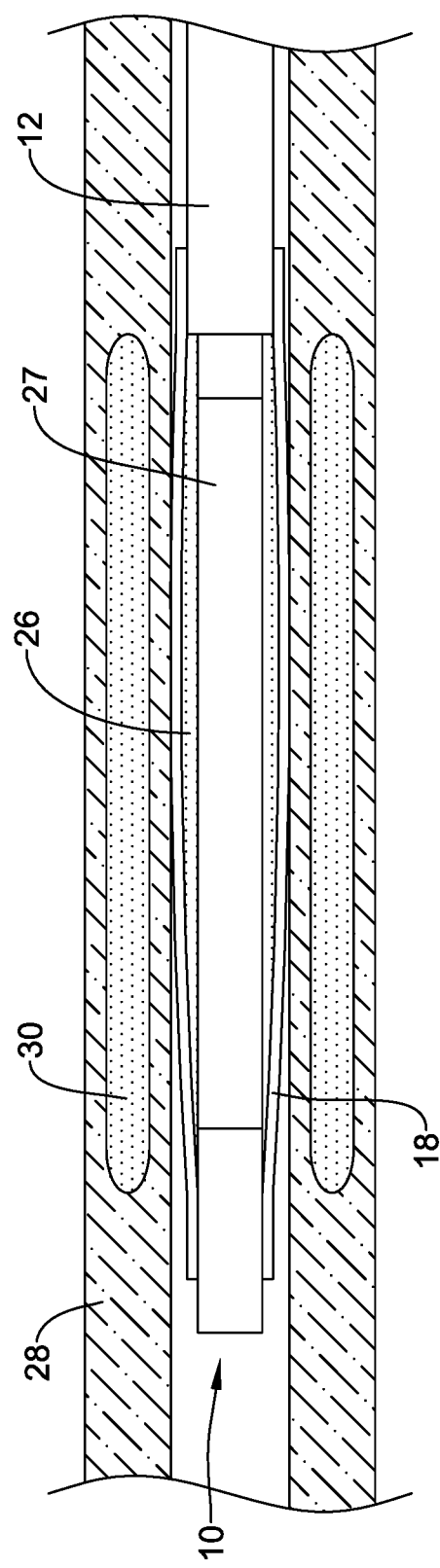
FIG. 3 is a partial cross-sectional side view of an example medical device disposed in a blood vessel.
Figure 4:
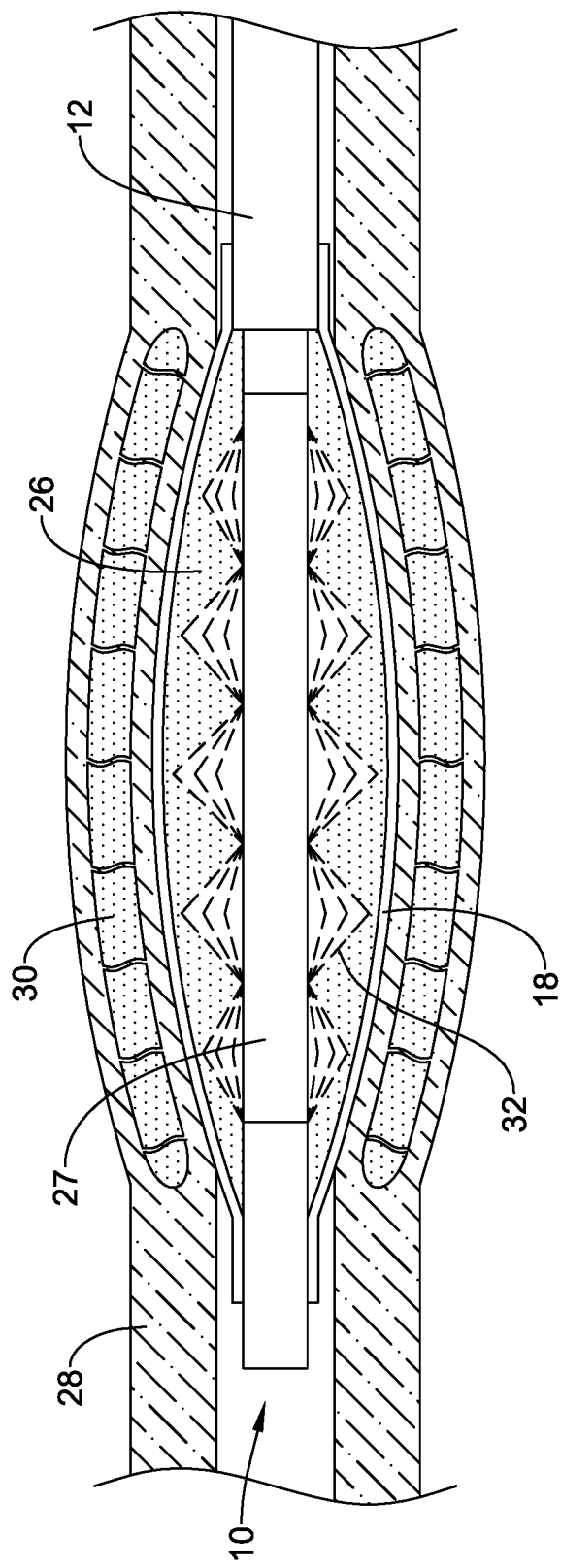
FIG. 4 is a partial cross-sectional side view of an example medical device disposed in a blood vessel.

The medical device 10 may be advanced through the blood vessel 28 to a position adjacent to the calcified lesion 30 as shown in FIG. 3. When suitably positioned, the balloon 18 may be partially inflated as schematically depicted in FIG. 4. Partially inflating the balloon 18 may occur by infusing an inflation media into the balloon 18 (e.g., via an inflation lumen that may be defined between the outer member 14 and the inner member 16. Partially inflating the balloon 18 may include inflating the balloon 18 so that the balloon 18 comes into contact with the wall of the blood vessel 28. This may include simply contacting the vessel wall or, in some instances, partially inflating the balloon 18 may include partially expanding the blood vessel 28. In some instances, partially inflating the balloon 18 may include inflating the balloon 18 to a first pressure that might be in the range of about 1-6 atmospheres or about 3-5 atmospheres.

With the balloon 18 partially inflated, the electrode 27 (and/or a suitable magnetic field generator) may be activated. Activating the electrode 27, including pulsing the electrode in order to pulse the magnetic field, may create a force or pulses of force 32 that can be transferred to the calcified lesion 30. For example, the pulsed magnetic field may cause the iron particles within the iron containing fluid 26 to migrate within the balloon 18, for example toward the surface of the balloon 18, so that pulses of force 32 may be transferred to the calcified lesion 30. The transferred forces may contact and break up the calcified lesion 30 as depicted in FIG. 4.

Figure 5:
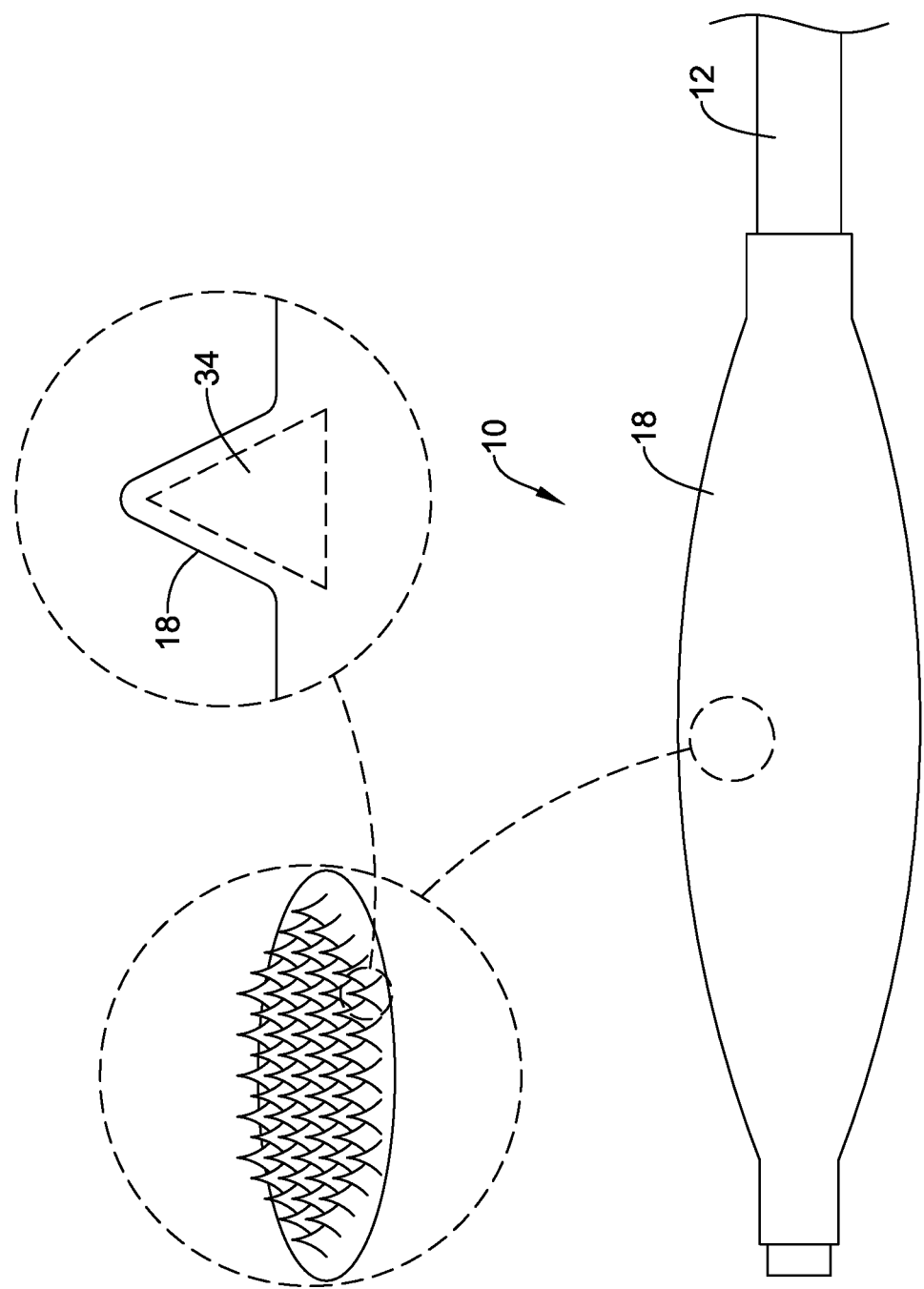
FIG. 5 is a side view of an example medical device.

As indicated above, the iron containing fluid 26 may include a plurality of nanoparticles, labeled in FIG. 5 with reference number 34. The nanoparticles 34 may have a variety of shapes. Some of the shapes contemplated include conical, geometric (e.g., having 3, 4, 5, 6, 7, 8, or more sides either regularly disposed or irregularly disposed), rounded or circular, oval, irregular, or the like. In at least some instances, the nanoparticles 34 may have a shape that allows the nanoparticles to protrude into the wall of the balloon 18 in a manner that deflects the wall of the balloon 18 in a corresponding manner. Thus, when the electrode 27 (and/or other magnetic field generators) is activated, the nanoparticles 34 can migrate to the surface of the balloon 18 and protrude into the wall of the balloon 18. These protrusions can engage the wall of the blood vessel (e.g., the blood vessel 28) and help to break up the calcified lesion 30. The reinforcing member 29 (e.g., best seen in FIG. 1) may help to fortify the balloon 18 so that the protrusion of the nanoparticles 34 into the wall surface of the balloon 18 does not puncture the balloon 18.

Figure 6:
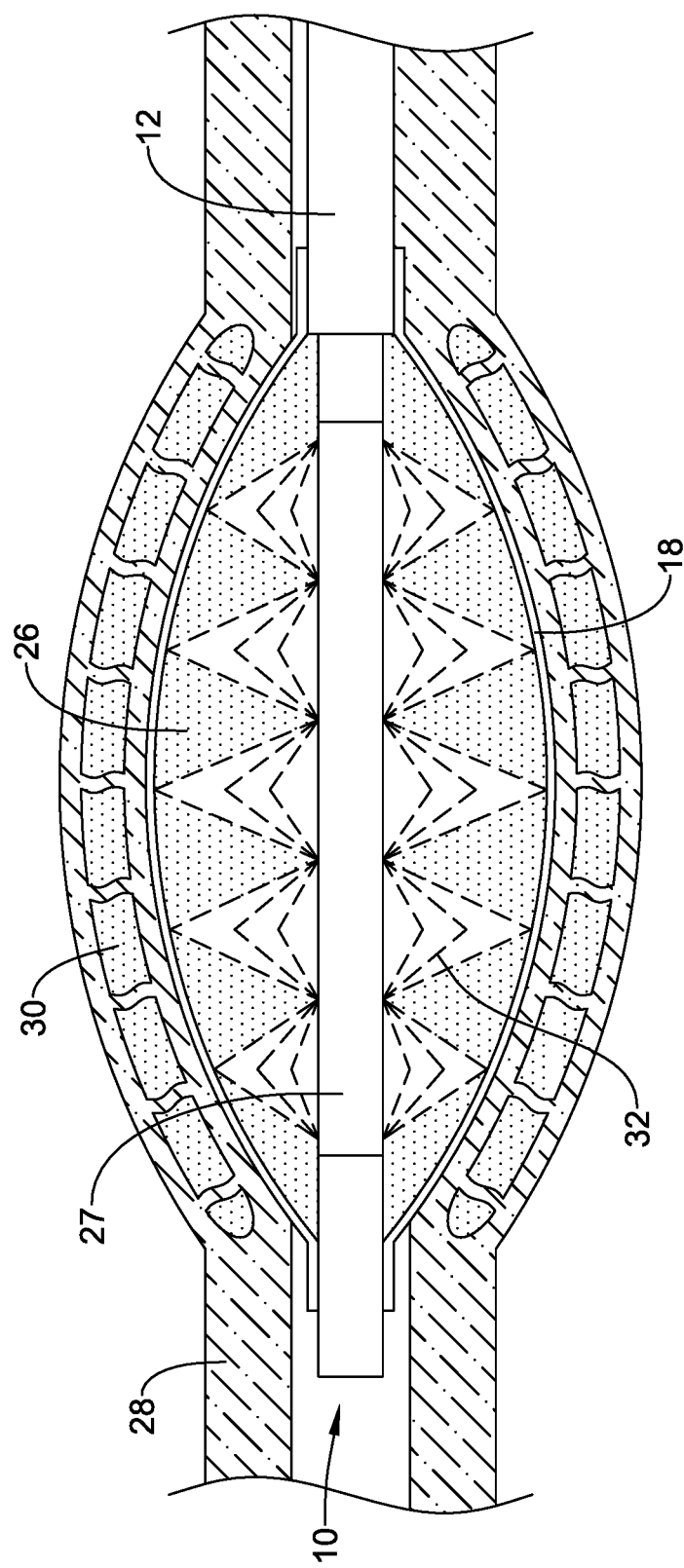
FIG. 6 is a partial cross-sectional side view of an example medical device disposed in a blood vessel.

With the calcified lesion 30 broken up, the balloon 18 may be further inflated to a second pressure, greater than the first pressure, to treat the blood vessel 28 as shown in FIG. 6. In some instances, the second pressure may be on the order of about 4-12 atmospheres or about 5-9 atmospheres.

The materials that can be used for the various components of the medical device 10 (and/or other medical devices disclosed herein) disclosed herein may include those commonly associated with medical devices. For simplicity purposes, the following discussion makes reference to the catheter shaft 12 and other components of the medical device 10. However, this is not intended to limit the devices and methods described herein, as the discussion may be applied to other similar tubular members and/or components of tubular members or devices disclosed herein.

The catheter shaft 12 and/or other components of the medical device 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the medical device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device 10 to achieve the same result.

In some embodiments, a degree of Magnetic Resonance Imaging (MRI) compatibility is imparted into the medical device 10. For example, the medical device 10, or portions thereof, may be made of a material that does not substantially distort the image and create substantial artifacts (e.g., gaps in the image). Certain ferromagnetic materials, for example, may not be suitable because they may create artifacts in an MRI image. The medical device 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A method for treating a blood vessel, the method comprising:
    disposing a medical device within the blood vessel at a position adjacent to a lesion, the medical device comprising:
        an elongate shaft having a distal end region, an electrode coupled to the shaft and positioned within the balloon,
        a balloon coupled to the distal end region, and
        an iron-containing fluid disposed within the balloon;
    inflating the balloon to a first pressure;
    delivering a plurality of electromagnetic pulses from the electrode to the iron-containing fluid; and
    inflating the balloon to a second pressure greater than the first pressure.

2. The method of claim 1, wherein the iron-containing fluid includes iron nanoparticles.

3. The method of claim 2, wherein at least some of the iron nanoparticles have a conical shape.

4. The method of claim 2, wherein delivering a plurality of electromagnetic pulses to the balloon moves at least some of the iron nanoparticles toward a surface of the balloon.

5. The method of claim 1, wherein an electrode is coupled to the shaft and positioned within the balloon, and wherein delivering a plurality of electromagnetic pulses to the iron-containing fluid includes activating the electrode.

6. The method of claim 1, wherein the balloon further comprises a reinforcing member.

7. The method of claim 1, wherein inflating the balloon to a first pressure includes inflating the balloon to a pressure of 3-5 atmospheres.

8. The method of claim 1, wherein inflating the balloon to a second pressure greater than the first pressure includes inflating the balloon to a pressure of 5-9 atmospheres.

9. A method for treating a blood vessel, the method comprising:
    disposing a lithotripsy angioplasty medical device within the blood vessel at a position adjacent to a calcified lesion, the lithotripsy angioplasty medical device comprising:
        an elongate shaft having a distal end region,
        a balloon coupled to the distal end region,
        an iron-containing fluid disposed within the balloon, and
        an electrode coupled to the shaft;
    inflating the balloon to a first pressure;
    transferring force from the balloon to the calcified lesion by delivering electromagnetic pulses with the electrode to activate the iron-containing fluid; and
    inflating the balloon to a second pressure greater than the first pressure.

10. The method of claim 9, wherein the iron-containing fluid includes iron nanoparticles.

11. The method of claim 10, wherein at least some of the iron nanoparticles have a conical shape.

12. The method of claim 11, wherein transferring force from the balloon to the calcified lesion by delivering electromagnetic pulses with the electrode to activate the iron-containing fluid moves at least some of the iron nanoparticles toward a surface of the balloon.

13. The method of claim 9, wherein the electrode is positioned within the balloon.

14. The method of claim 9, wherein the balloon further comprises a reinforcing member.

15. The method of claim 9, wherein inflating the balloon to a first pressure includes inflating the balloon to a pressure of 3-5 atmospheres.

16. The method of claim 9, wherein inflating the balloon to a second pressure greater than the first pressure includes inflating the balloon to a pressure of 5-9 atmospheres.

17. A lithotripsy angioplasty medical device, comprising:
    an elongate shaft having a distal end region;
    a balloon coupled to the distal end region;
    an iron-containing fluid disposed within the balloon;
    an electrode coupled to the shaft and positioned within the balloon, the electrode being configured to deliver electromagnetic pulses to the fluid;

wherein the balloon is configured to shift between a first unexpanded configuration, a second configuration when the balloon is partially expanded into contact with a target region, and an expanded configuration.

18. The lithotripsy angioplasty medical device of claim 17, wherein the iron-containing fluid includes iron nanoparticles.

19. The lithotripsy angioplasty medical device of claim 18, wherein at least some of the iron nanoparticles have a conical shape.

20. The lithotripsy angioplasty medical device of claim 17, wherein the balloon further comprises a reinforcing member.

* * * * *